United States Patent [19]

Graham et al.

[11] Patent Number: 4,645,340
[45] Date of Patent: Feb. 24, 1987

[54] OPTICALLY REFLECTIVE SPHERE FOR EFFICIENT COLLECTION OF RAMAN SCATTERED LIGHT

[75] Inventors: Daniel J. Graham, Watertown, Mass.; Richard A. Mushlin, Ridgefield, Conn.

[73] Assignee: Boston University, Boston, Mass.

[21] Appl. No.: 499,804

[22] Filed: Jun. 1, 1983

[51] Int. Cl.⁴ .............................................. G01J 3/44
[52] U.S. Cl. .................................................... 356/301
[58] Field of Search ............... 356/236, 301, 338, 342; 250/228, 574

[56] References Cited

U.S. PATENT DOCUMENTS

| | | | |
|---|---|---|---|
| 2,925,007 | 2/1960 | Silver | 356/338 |
| 3,319,071 | 5/1967 | Werth et al. | 356/236 |
| 3,349,665 | 10/1967 | Grosheim et al. | 356/236 |
| 3,561,744 | 6/1970 | Hinman et al. | 356/301 |
| 3,704,951 | 12/1972 | Chupp | 356/301 |
| 3,806,727 | 4/1974 | Leonard et al. | 250/301 |
| 4,012,144 | 3/1977 | Hedelman | 250/228 |
| 4,071,298 | 1/1978 | Falconer | 356/73 |
| 4,088,407 | 5/1978 | Schoeffel et al. | 250/576 |
| 4,127,329 | 11/1978 | Chang et al. | 356/301 |
| 4,250,394 | 2/1981 | O'Connor | 356/340 |
| 4,310,246 | 1/1982 | Blazek | 356/236 |
| 4,395,126 | 7/1983 | Kramer | 356/417 |
| 4,405,237 | 9/1983 | Manuccia et al. | 356/301 |

FOREIGN PATENT DOCUMENTS 0015170 9/1980 France ............................... 356/325
0080039 6/1980 Japan ................................. 356/338

OTHER PUBLICATIONS

IBM Technical Disclosure Bulletin, "Variable Angle Reflectometer," G. M. DiGiacomo, vol. 20, N. 11A, Apr. 1978, pp. 4509-4510.
"Instrumentation for Raman/Rayleigh Light Scattering Measurements of Gas Densities and Temperatures in Aerospace Test Facilities," Powell, H. M. et al *ISA Transactions*, vol. 17, N. 2, 1978, pp. 69-85.
Ware, W. R. and Rothman, W., "Relative Fluorescence Quantum Yields Using an Integrating Sphere, The Quantum Yield of 9,10-Diphenylanthracene in Cyclohexane" *Chem. Phys. Lett.* 39, 449 (1976).

*Primary Examiner*—F. L. Evans
*Assistant Examiner*—Joel L. Harringa
*Attorney, Agent, or Firm*—Hamilton, Brook, Smith & Reynolds

[57] ABSTRACT

A device for the collection of Raman scattered light by means of an internally reflective sphere 10 wherein a light source 12 provides light to and through a sample 16, which light is reflected back through that sample by the internally reflective sphere 10. The sample is viewed by means of a spectrograph 30 focused by lenses 26, 28 or a fiberoptic light pipe 46.

11 Claims, 3 Drawing Figures

4,645,340

OPTICALLY REFLECTIVE SPHERE FOR EFFICIENT COLLECTION OF RAMAN SCATTERED LIGHT

TECHNICAL FIELD

This invention relates to the spectral analysis of light and is particularly useful in the collection of Raman scattered light.

BACKGROUND OF THE INVENTION

Various optical configurations utilizing one or more concave mirrors and lenses have been used for many years in collecting the inelastically scattered light which is observed upon nearly monochromatic irradiation of material samples. This inelastic scattering of light, or the Raman effect, is characterized by changes in the radiation frequency which are usually on the order of molecular vibrational frequencies. Such Raman scattered light contains a wealth of electronic and vibrational information, although it is usually of very weak intensity compared with that of the radiation source. In fact, the Raman scattered/source light intensity ratio is typically in the order of $10^{-6}$ or less. It is because the inelastically scattered light is of such weak intensity that Raman scattering experiments are often characterized by both non-trivial experimental procedures and expensive equipment. In particular, the commercially available optical systems which facilitate the detection and analysis of inelastically scattered light are rather complicated and very expensive.

In a typical optical arrangement associated with a sample mount, nearly monochromatic light, such as from a laser, is passed through a double convex lens which focuses the light upon the material sample. In spectral regions in which the sample (e.g. a liquid) is relatively transparent with respect to the source radiation, most of the light which passes through the sample can be reflected by a concave mirror back through the sample towards the light source. In this experimental configuration, the source light effectively passes twice through the sample in order to double the source radiation intensity. The source light is then subject to both elastic and inelastic scattering which can be observed at an angle with respect to the source beam path. The elastic and inelastic scattering events represent, respectively, light deflected by the sample of frequency equal to that of the source, and light deflected by the sample of frequency different from that of the source. Typically the detection path is perpendicular to that of the path of incidence; a concave mirror and a convex lens are placed along the detection path at opposite sides of the sample at distances from the sample equal to their respective focal lengths. The collection optics serve to focus the scattered light upon the aperture of a spectrograph. This latter instrument enables the frequency analysis of the inelastically scattered radiation. The concave mirror serves to reflect some of the scattered light which originates from the sample traveling in directions other than that of the lens/spectrograph. The purpose of the mirror is thus to reflect some of this scattered light back through the sample, through the lens, and finally to the spectrograph such that the signal intensity is indeed enhanced. It is noted that light collection setups are typically at right angles to the light source so that the high intensity source light (i.e., as that from a laser) is not accidentally channeled to the spectrograph where it may inflict damage to the gratings and detection electronics.

There are several types of problems with the current commercially availabe scattered radiation collection systems. One problem is that the concave mirror placed in back of the sample, due to its limited surface area, reflects only a small portion of the total amount of scattered light toward the lens/spectrograph. Thus much of the scattered light escapes detection.

Another problem with the commercial devices is that they usually lack in versatility. The commercially available sample mounts are often difficult to interface with an existing spectrograph on hand in one's laboratory. In addition, extra components must be purchased in order to accommodate samples of various morphologies and effect low temperature experimental capabilities. Such optional equipment greatly increases the financial outlay requirements of an already expensive optical detection system.

The primary object of this invention is to provide a versatile and efficient collector of scattered radiation which can be inexpensively constructed.

DISCLOSURE OF THE INVENTION

The invention makes use of an internally optically reflective sphere for the collection of scattered light and the analysis thereof. The sphere has an opening to allow for the placement of a material sample in its center. Openings are also made for the introduction of light to illuminate the sample and for observation of the illuminated sample by means of a spectrograph.

The above-mentioned sphere may be of glass having an inside surface coated with a highly reflected metallic film (e.g. aluminum). Lenses may be used with the sphere for scattered light collection. A lens of focal length approximately equal to the radius of the sphere is used to conduct scattered light for spectrographic analysis. Alternatively, a fiberoptic light pipe might be abutted to the sample in order to conduct light for spectrographic analysis.

An alternative embodiment of the invention makes use of two concave mirrors external to the sphere. Nearly monochromatic light (i.e. from a laser) passes through the sample and then out of the sphere and externally about the sphere for reintroduction to the sphere at a displaced position. The light then reintroduced into the sphere travels through the sample once again and is then reflected back again by a focusing mirror. In this way the light may be conducted through the sample several times.

An advantage of this device is an increase in efficiency gained through the use of a sphere for collection of scattered light. The increased efficiency results from the multiple reflections of a large portion of source radiation which would otherwise be lost from the system by means of the internal surface of the sphere. This source radiation is reflected repeatedly back to the sample where it may induce Raman scattering processes. In addition, the inelastically scattered light which is not at first directed to the spectrograph may, after several reflections within the sphere, finally be detected. Such a configuration greatly enhances the detected signal intensity of inelastically scattered light. This sphere is easier to position and align with respect to the spectrograph than most commercially available optical systems. Another advantage is the relative inexpensiveness of this device as compared to currently available collection optics. Furthermore, the sphere is easier to position and align than most conventional mirror and lens systems.

BRIEF DESCRIPTION OF THE DRAWINGS

The foregoing and other objects, features, and advantages of the invention will be apparent from the following more particular description of the preferred embodiments of the invention as illustrated in the accompanying drawings in which like reference characters refer to the same parts throughout the different views. The drawings are not necessarily to scale, emphasis instead being placed upon clearly illustrating the principles of the invention.

DESCRIPTION OF PREFERRED EMBODIMENTS OF THIS INVENTION

Figure 1:
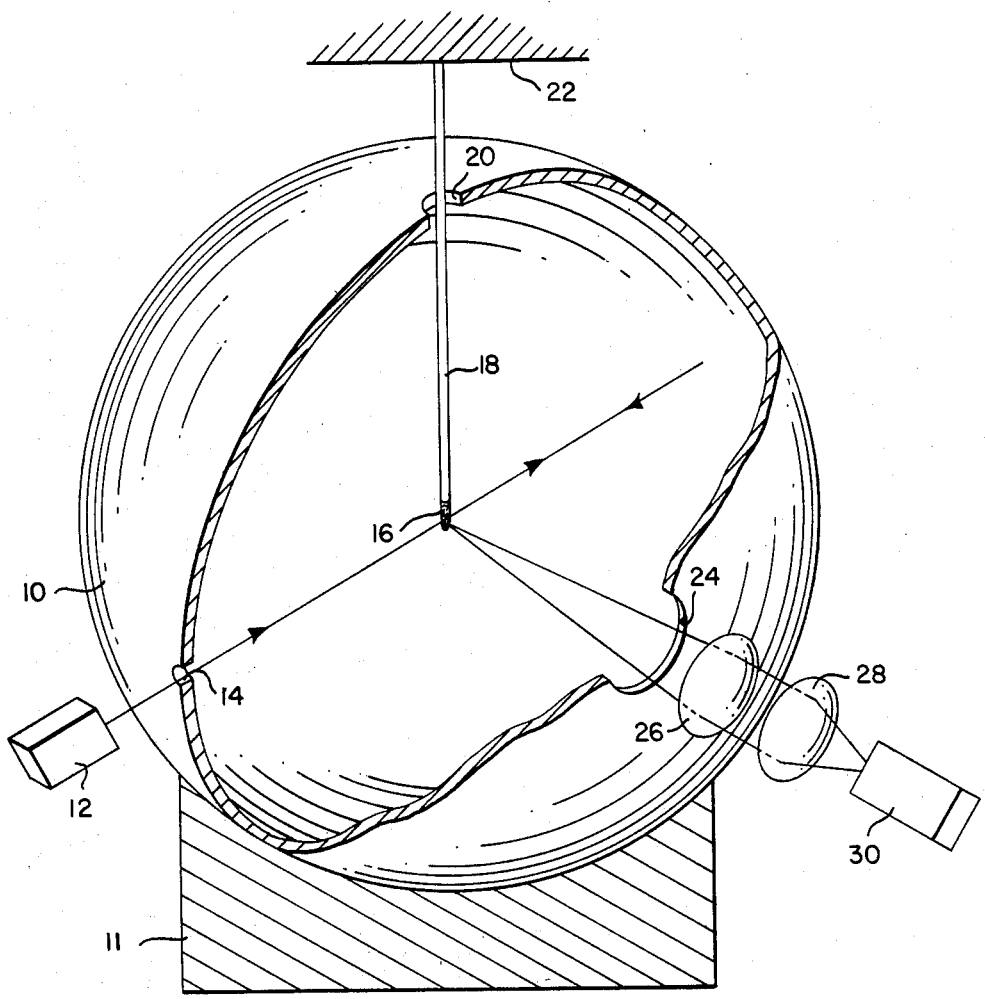
FIG. 1 is a perspective view of a light collection device in which an internally mirrored sphere is utilized for passing monochromatic light through a material sample and collecting scattered light for analysis.

FIG. 1 is a cutaway view of a large internally reflective sphere 10. The sphere is held in a multipoint support cradle which may be a stand with at least three arms or a cup 11 with an inner diameter comparable to the sphere's outer diameter. The multipoint support cradle allows for the precise adjustment of sphere position relative to a light source and a spectrograph.

The sphere 10 has various ports which allow the device to be used as a collector for elastic and inelastically scattered light. Laser light from a laser 12 is introduced through hole 14. The laser light passes through the sphere 10 and encounters the material sample 16 whose area cross section is approximately equal to that of the laser. The material sample is positioned in the center of the sphere at the end of a pipette or rod 18 which protrudes through the sphere by way of hole 20. The sphere is held stationary with respect to stand 22 and the sample by the cradle 11 in which the sphere is held.

The passing of light through the sample 16 produces four forms of scattered light. Light scattered by the sample passes through hole 24 and is focused upon the spectrograph 30 through lenses 26 and 28. The spectrograph sees the four different forms of light: (1) light elastically scattered by the sample with no mediation by the reflecting surface, (2) light elastically scattered by the sample with mediation by the reflecting surface, (3) light inelastically scattered by the sample with no mediation by the reflecting surface, and (4) light inelastically scattered by the sample with mediation by the reflecting surface. No direct laser light is seen by the spectrograph since the sensed light is at right angles from the sample and laser beam.

As the focal point of the sphere lies at its center at which is placed the sample, a large portion of the light which does not exit through hole 24 is reflected back to the sample. Thus, light is repeatedly passed through the sample to make efficient use of the available laser light. A very small portion of that light is shifted in frequency due to the Raman effect, and a portion of the Raman light is detected through the hole 24 by the spectrograph 30. An efficient sampling of the scattered light is achieved via a lens 26 whose focal length is approximately equal to the radius of the sphere so that only light from the sample is primarily viewed by the lens 26, as shown in FIG. 1.

The physics behind the reflective sphere can be understood on an elementary level according to the principles of geometric optics. The multiple passings of the laser beam and the multiple reflections of Rayleigh (elastic) and Raman (inelastic) scattered light back to the sample account for the increased collection efficiency.

An optional fourth hole which is not shown may be cut in the sphere so as to accommodate the tail of a low temperature cryostat. This configuration would allow efficient light scattering experiments at low temperatures.

The embodiment as described above has been successful in inexpensively yielding results similar to the most expensive mirror and lens apparatus in prior use. The following alternate embodiment enhances the collection of Raman light even further.

Figure 2:
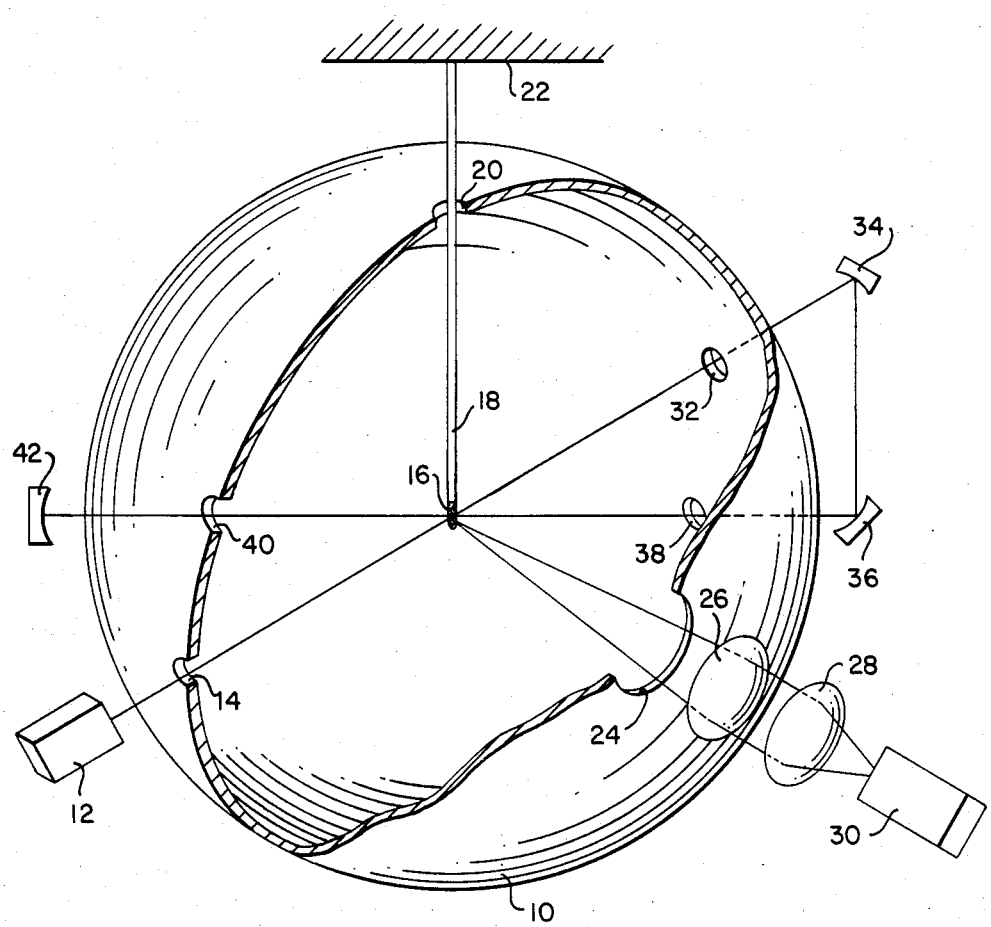
FIG. 2 is an alternate mode of operation of the invention in which a mirrored sphere is so arranged in conjunction with a laser light beam and confocal mirror that the laser beam is reflected through the sample a multitude of times.

Referring now to FIG. 2, a laser 12 is so positioned that the light emitted goes through hole 14 in the sphere 10 and on through the sample 16 and then out through hole 32. The laser light is reflected by concave mirror 34 outside the sphere to concave mirror 36. The light is then projected through hole 38 and back through the sphere to the sample 16. On leaving the sample the second time, the light proceeds through hole 40 to another concave mirror 42. Concave mirror 42 focuses the beam back upon the sample 16. Much of the laser light thus projected is reflected through the sample many times.

The total amount of scatter light is increased by the numerous re-reflections of the laser light through the sample. Some of this scattered light passes both directly and by reflection through hole 24. Convex lenses 26 and 28 serve to focus the scattered light upon the aperture of the spectrograph 30. In this embodiment, as in the previous embodiment, the spectrograph may be set to measure the wavelength of the inelastically scattered light.

In this embodiment, as in the previous embodiment, the sample is held by a pipette or rod 18 positioned through hole 20 from a stand 22. The stand holding the sphere is not shown. An additional hole may be added to the sphere as suggested above for the accommodation of a low temperature cryostat.

Figure 3:
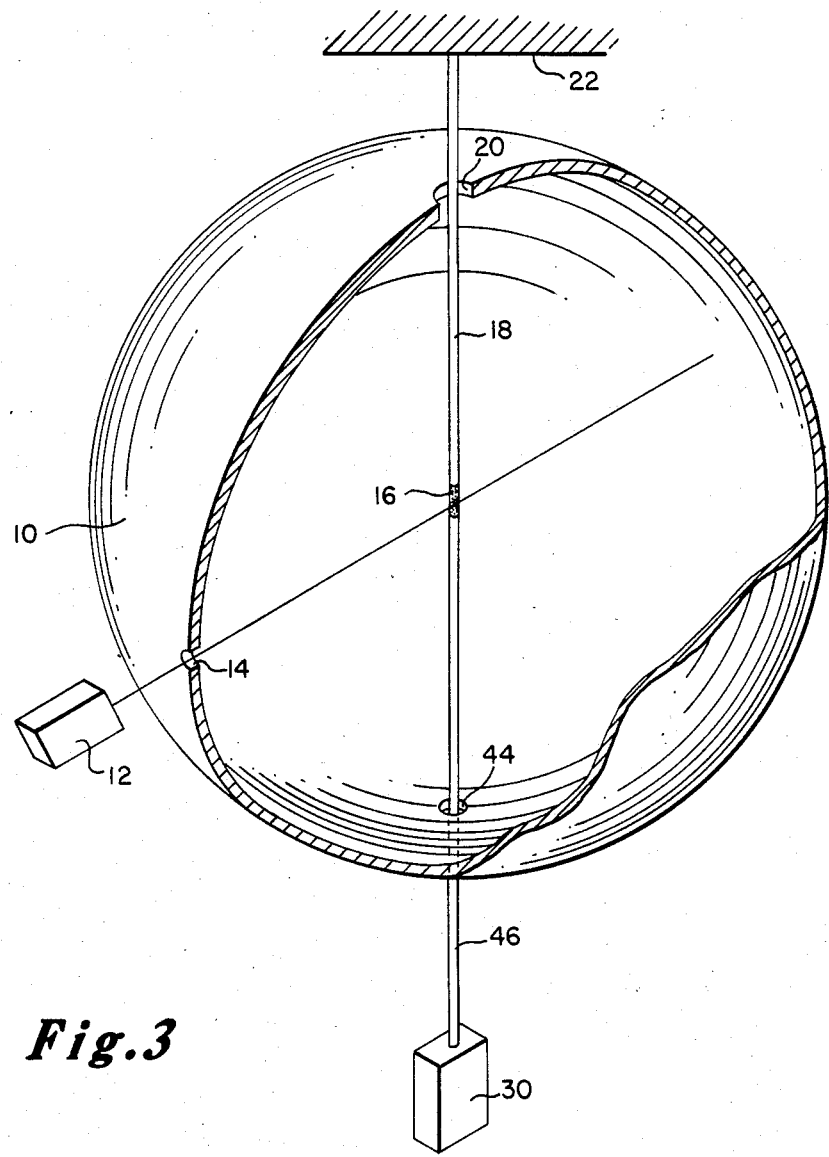
FIG. 3 is an alternate embodiment of this invention in which a light pipe is mounted between the spectrograph and material sample for efficient collection of scattered light.

The laser arrangement as discussed above can be used to increase light intensity across the sample by reflection of the laser light many times through the sample. This arrangement may also be used in the alternate embodiment which will be described below and is shown in FIG. 3. This is to say that the embodiments shown in FIG. 2 and FIG. 3 may be combined into a single embodiment comprised of the novel aspects of each.

In FIG. 3 the spherical bulb is similar to those shown in FIGS. 1 and 2. The salient difference is that a light pipe 46, which may comprise single or multiple fiber optic filaments, is used to connect the material sample 16 optically with the spectrograph 30.

The light pipe 46 is placed through hole 44 and connected directly to the sample 16 and to the spectrograph 30. The sample is held by pipette or rod 18 positioned through hole 20 from stand 22. The sphere 10 in this figure is laid out much as it is in FIG. 1. The laser 12 shines through hole 14, and through the material sample 16. It is reflected back by the internal surface of the spherical globe once again encountering the sample 16. The light which is not scattered then travels out of the globe through hole 14, not to return to the sample. The alternate arrangement of the laser and mirrors as shown in FIG. 2 above works equally well with the proper placement of the light pipe so that it does not receive direct laser light.

An advantage of using the light pipe shown in FIG. 3 is that it minimizes alignment problems. The lenses as used in FIG. 1 and FIG. 2 must be carefully aligned so as to deliver the scattered light to the aperture of the spectrograph. Further, the light pipe is an efficient collector of light from the sample.

While the invention has been particularly shown and described with reference to preferred embodiments thereof, it will be understood by those skilled in the art that various changes in form or details may be made therein without departing from the spirit and scope of the invention as described by the intended claims. For example, various combinations of lenses and mirrors may be used to focus laser or monochromatic light across a sample.

We claim:

1. A device for Raman scattered light collection and analysis characterized by:
   a. an internally optically reflective sphere having an illuminating aperture and a detection aperture therein;
   b. means for placing a material sample entirely in the center of the sphere;
   c. means for illuminating the material sample through the illuminating aperture such that light is redirected through the sample with reflection from the sphere; and
   d. detecting means for detecting Raman scattered light which is directed radially outward from the sample through the detection aperture toward the detecting means.

2. A device as claimed in claim 1 wherein the sphere is constructed of glass and where the inside surface of the glass is coated with a reflective film so that the interior of the sphere is highly reflective to light.

3. A device as claimed in claim 1 wherein the sphere is supported by a multipoint cradle.

4. A device as claimed in claim 1 wherein the means for illuminating is a nearly monochromatic light source.

5. A device as claimed in claim 1 or 2 wherein Raman scattered light is collected by a light pipe for analysis and conveyed to a spectrum analyzer by the light pipe.

6. A device as claimed in claim 1 or 2 wherein at least one lens of focal length approximately equal to the radius of the sphere is used to collect Raman scattered light for spectroscopic analysis.

7. A device for Raman scattered light collection and analysis comprising:
   an internally optically reflective sphere;
   means for placing a material sample in the center of the sphere;
   means for illuminating the material sample through a first pinhole in the sphere;
   a second pinhole diametrically opposite the first pinhole and light source;
   a first concave mirror outside of the sphere behind said second pinhole;
   a third pinhole displaced from the first and second pinholes;
   a second concave mirror outside of the sphere behind said third pinhole, the third pinhole and the second mirror being positioned such that the second mirror receives light from the first concave mirror and reintroduces it through the third pinhole into the sphere directed toward the sample; and
   means for detecting Raman scattered light from the sample.

8. A device for Raman scattered light collection and analysis comprising:
   an internally optically reflective sphere;
   means for placing a material sample in the center of the sphere;
   means for illuminating the material sample through a first pinhole in the sphere;
   a second pinhole diametrically opposite the first pinhole and light source;
   a first concave mirror outside of the sphere behind said second pinhole;
   a third pinhole displaced from the first and second pinholes;
   a second concave mirror outside of the sphere behind said third pinhole, the third pinhole and the second mirror being positioned such that the second mirror receives light from the first concave mirror and reintroduces it through the third pinhole into the sphere directed toward the sample;
   a fourth pinhole opposite said third pinhole;
   a mirror positioned outside of the sphere behind said fourth pinhole to receive light from the second mirror and focus the light back through the fourth pinhole onto the material sample; and
   means for detecting Raman scattered light from the sample.

9. A method of analyzing Raman light scattered by a material sample comprising:
   placing a material sample entirely at the center of an internally, optically reflective sphere;
   shining light through the material sample and redirecting light through the sample with reflection from the sphere; and
   through an aperture in the sphere detecting Raman light scattered and directed radially outward from the sample.

10. A method of analyzing Raman light scattered by a material sample as claimed in claim 9 wherein the Raman scatterd light is detected through a light pipe placed between the sample on one end and a spectrograph at the other end.

11. A method of analyzing Raman light scattered by a material sample as claimed in claim 9 wherein laser light is shown through the material sample.

* * * * *